United States Patent [19]

Lekholm

[11] Patent Number: 5,730,119
[45] Date of Patent: Mar. 24, 1998

[54] METHOD AND DEVICE FOR IDENTIFYING ANAESTHETIC IN AN ANAESTHETIC SYSTEM

[75] Inventor: Anders Lekholm, Bromma, Sweden

[73] Assignee: Siemens Elema AB, Solna, Sweden

[21] Appl. No.: 583,622

[22] Filed: Jan. 5, 1996

[30] Foreign Application Priority Data

Jan. 19, 1995 [SE] Sweden ............................ 9500175

[51] Int. Cl.$^6$ ............................ G01N 25/68; A61M 16/01
[52] U.S. Cl. .................... 128/200.24; 128/203.27; 128/203.26; 128/203.25; 128/203.17; 128/203.16; 128/203.12
[58] Field of Search ................. 128/203.12, 203.14, 128/203.16, 203.17, 203.25, 203.26, 203.27, 202.27, 200.24; 261/39.1, 96, 99, 405, DIG. 65; 374/16–28

[56] References Cited

U.S. PATENT DOCUMENTS

| | | | |
|---|---|---|---|
| 3,581,554 | 6/1971 | LaFitte et al. | 374/19 |
| 3,937,059 | 2/1976 | Nisolle | 374/21 |
| 4,083,224 | 4/1978 | Gayst | 374/19 |
| 4,730,478 | 3/1988 | Gedeon | 73/23.21 |
| 5,272,907 | 12/1993 | Hakala | 73/23.2 |

FOREIGN PATENT DOCUMENTS

| | | |
|---|---|---|
| 0 553 789 | 8/1993 | European Pat. Off. |
| 3915018 | 11/1990 | Germany . |
| 2 029 572 | 3/1980 | United Kingdom . |
| 2 224 849 | 8/1991 | United Kingdom . |

*Primary Examiner*—V. Millin
*Assistant Examiner*—William J. Deane, Jr.
*Attorney, Agent, or Firm*—Hill, Steadman & Simpson

[57] ABSTRACT

For preventing a patient from being administered an erroneous anaesthetic, an incorrect concentration of anaesthetic or a mixture of anaesthetics, an anaesthetic system is equipped with a device capable of identifying anaesthetics in the anaesthetic system. A device for simple and reliable identification of anaesthetics does so by having a thermal element which varies the temperature of at least some of the anaesthetic to cause it to undergo a change in physical state, e.g., condensation from the gaseous state to the liquid state. A transition temperature at which the change in physical state occurred is determined and the anaesthetic is identified from the determined transition temperature. The condensation point temperature can be determined by sensing the capacitance between two conductors or sensing changes in the resonant behavior of an oscillating crystal.

16 Claims, 3 Drawing Sheets

METHOD AND DEVICE FOR IDENTIFYING ANAESTHETIC IN AN ANAESTHETIC SYSTEM

BACKGROUND OF THE INVENTION

1. Field of the Invention

The present invention relates to a method and a device for identifying at least one anaesthetic in an anaesthetic system.

2. Description of the Prior Art

In general, placing a patient in a state of anaesthesia, or narcosis, means that the patient is rendered unconscious and unable to feel any pain. Usually, a mixture of oxygen, nitrous oxide, an anaesthetic gas and possibly air is supplied to the patient via a breathing circuit in an anaesthetic system. The most common anaesthetic gases are halothane, desflurane, enflurane, isoflurane and sevoflurane. The anaesthetic is normally in a liquid state in an anaesthetic vaporizer in the anaesthetic system and a desired amount of anaesthetic gas is vaporized from the liquid and delivered to the breathing circuit as anaesthesia is induced in the patient.

Different anaesthetics, which are administered in different concentrations, have different effects on the patient. The side-effects of different anaesthetics also differ. Anaesthetic systems are thus available which can be equipped with a number of anaesthetic vaporizers enabling the anaesthetist to choose the anaesthetic he or she deems best for the patient, without any need to connect or detach different anaesthetic vaporizers during surgery. This may be the case e.g. in surgery on children or in an operation of long duration.

A mixture of different anaesthetics, however, should not be supplied to the patient, since the effect of such a mixture is unpredictable and largely unknown. The anaesthetic system, therefore, must be devised so that only one anaesthetic at a time can be supplied to the patient. It is possible, however, that a number of anaesthetic gases could become mixed, even in an anaesthetic system which utilizes only one anaesthetic vaporizer, such as when the active anaesthetic vaporizer is filled with anaesthetic.

In order to minimize the risk of errors in the administration of anaesthetics, it would be advantageous if the anaesthetic system were capable of automatically identifying the anaesthetic administered to the patient. With such a capability, the anaesthetic system then could be devised to stop the supply of anaesthetic to the patient, if an error occurs, and simultaneously warn staff of the error.

As noted above, the different known anaesthetics can be supplied to the patient in different concentrations. If an incorrect concentration is set for a particular anaesthetic, the patient could be subjected to needless risks, i.e. 20 overdosage or underdosage of the anaesthetic. This would also be the case if an incorrect anaesthetic were supplied.

These risks also would be greatly reduced if the anaesthetic could be identified before being supplied to the patient.

In the field of anaesthesia, the identification of anaesthetic with optical methods is known, i.e., using absorption spectrometry. Since many anaesthetics have a similar absorption spectrum, absorption must be measured at a number of different wavelengths in order to make a distinguishing identification. This makes expensive, complex equipment necessary for identifying anaesthetics. Optical measurements are generally performed on the gas mixture supplied to the patient, i.e., with the anaesthetic in a gaseous state.

Another known way of identifying an anaesthetic is based on the use and combination of two different measurement methods for determining the concentration of the anaesthetic as well as for identifying the anaesthetic. An optical method could be used for measuring the anaesthetic at a specific wavelength, and measurement could be made with an oscillating crystal coated with a layer of oil or grease which absorbs and resorbs the anaesthetic gas. Depending on the molecular weight and concentration of the anaesthetic, the crystal's oscillation frequency changes to varying degrees. A combination of these two measurement methods yields a unique signal for every known anaesthetic. It should be noted that measurement using changes in crystal frequency only, is not in itself sufficient for identifying anaesthetics, since the frequency change is identical for the different anaesthetics at the concentrations in which they are used. One such device is described in U.S. Pat. No. 5,272,907.

SUMMARY OF THE INVENTION

An object of the present invention is to provide a method for identifying an anaesthetic in anaesthetic system in a simple and reliable manner.

Another object is to provide a device for use in anaesthetic system for identifying at least one anaesthetic in the anaesthetic system.

The first object is achieved in accordance with the invention by a procedure having the following methodological steps.

The temperature of at least some of the anaesthetic is varied, so it changes from a first physical state to a second physical state.

A determination is made of a transition temperature at which the change occurs.

The anaesthetic is then identified from the transition temperature thus determined.

Even if different anaesthetics have similar properties, they change to different physical states at different temperatures, a circumstance the present invention utilizes for identifying them.

The term "physical state" as used herein means a state wherein the anaesthetic has a particular internal energy which thermodynamically defines its state function. The only criteria for distinguishing between the aforementioned first and second physical states is thus that they have a measurable relative difference in internal energy, however manifested. Although phases (gas, liquid, solid) are the most common physical states, the method (and apparatus) can make use of any change from any physical state to another which exhibits a measurable change in internal energy.

In a first embodiment of the method the first physical state is a gas, the second physical state is a liquid, and the transition temperature is a condensation point temperature, the temperature being varied such that at least some of the gaseous anaesthetic condenses, the condensation point temperature being determined, and the anaesthetic being identified from the determined condensation point temperature. Immediately after the liquid anaesthetic has been vaporized, it is present in many instances in a wholly gaseous state, or saturated in a gas mixture. The anaesthetic can be reliably identified when the temperature of some of the vaporized anaesthetic is varied so the anaesthetic starts to condense and the temperature at which condensation takes place is simultaneously determined. If the anaesthetic is not present in a wholly gaseous state, or saturated in a gas mixture, the concentration must also be determined for reliable identification of the anaesthetic.

In a second embodiment of the method the first physical state of aggregation is a liquid, the second physical state is a solid and the transition temperature is a freezing point temperature, the temperature being varied such that at least some of the liquid anaesthetic freezes, the freezing point being determined and the anaesthetic being identified from the freezing point temperature determined.

It is preferable for only a small amount of liquid anaesthetic to be diverted from the vaporizer and cooled until it at least partially crystallizes into a solid. The freezing point temperature is unique for each anaesthetic, and identifying the anaesthetic from the determined freezing point temperature is therefore easy.

In a third embodiment of the method the first physical state is a liquid, the second physical state is a gas and the transition temperature is the boiling point temperature, the temperature being varied so at least some of the liquid anaesthetic boils, the boiling point temperature being determined and the anaesthetic being identified from the boiling point temperature determined.

In the corresponding manner as in the freezing of some of the liquid anaesthetic, preferably only a small amount of the liquid anaesthetic is extracted and heated to the boiling point. The boiling point temperature can be determined in a number of ways. For example, the pressure in the heated liquid anaesthetic can be measured. A relatively large increase in pressure occurs when the boiling point is reached.

A device for identifying anaesthetics in accordance with the invention has a control unit, a thermal element controlled by the control unit for varying the temperature of at least some of the anaesthetic so it changes from a first state of aggregation to a second state of aggregation, and a physical state-sensitive means for determining the temperature at which the transition occurs, the anaesthetic being identified from the determined temperature.

The device can suitably be devised to perform one of the above three methods, viz. to determine a condensation point temperature, a freezing point temperature or a boiling point temperature.

One suitable way for determining when condensation occurs can be achieved using a condensation point detector which measures a change in some electrical property which involves the anaesthetic, preferably capacitance, between two parallel conductors, caused by condensation on the surface of the condensation point detector. Capacitance increases when condensation takes place. The temperature of the thermal element when this occurs is then defined as the condensation point temperature. Alternatively, a number of measurements of condensation point temperatures can be made and an average value calculated from which the anaesthetic can be identified.

Another suitable technique for determining when condensation occurs is achieved using a condensation detector formed by an oscillating (excited) crystal on which the gaseous anaesthetic condenses, a detectable change in the crystal's resonant frequency then occurring. It should be noted that absorption of anaesthetic is not involved here, as is the case in determinations of concentration with oscillating crystals (described in the earlier discussion of the state of the art). A number of measurements can also be made and an average value calculated.

Yet another way to devise the device to determine when condensation occurs is achieved in a condensation detector with an optical detector. The optical detector can sense changes in a light beam reflected from a reflective surface on which condensation occurs. Alternatively, the optical detector can sense changes in a light beam transmitted through a transparent surface on which condensation occurs. Performing a number of measurements and calculating an average value for the condensation point temperature is more important in optical determinations than in other determinations.

When the above determinations are made for a gaseous anaesthetic, the device can be placed in a breathing circuit in the anaesthetic system, and a concentration meter can be arranged in the breathing circuit to measure the concentration of the anaesthetic, identification of the anaesthetic being made at the same time from the condensation point temperature and the measured concentration.

Simultaneous measurement of the concentration of anaesthetic is also necessary when an anaesthetic is identified by determination of the condensation point temperature in a part of the anaesthetic system in which the concentration of anaesthetic is not completely known, since the concentration influences the partial pressure of an anaesthetic in the gaseous state and, in turn, influences the condensation point temperature. As previously noted, this measurement can advantageously be made at a point in the anaesthetic system at which the anaesthetic is in a wholly gaseous state, or saturated, at which concentration does not have the same impact.

DESCRIPTION OF THE PREFERRED EMBODIMENTS

Figure 1:
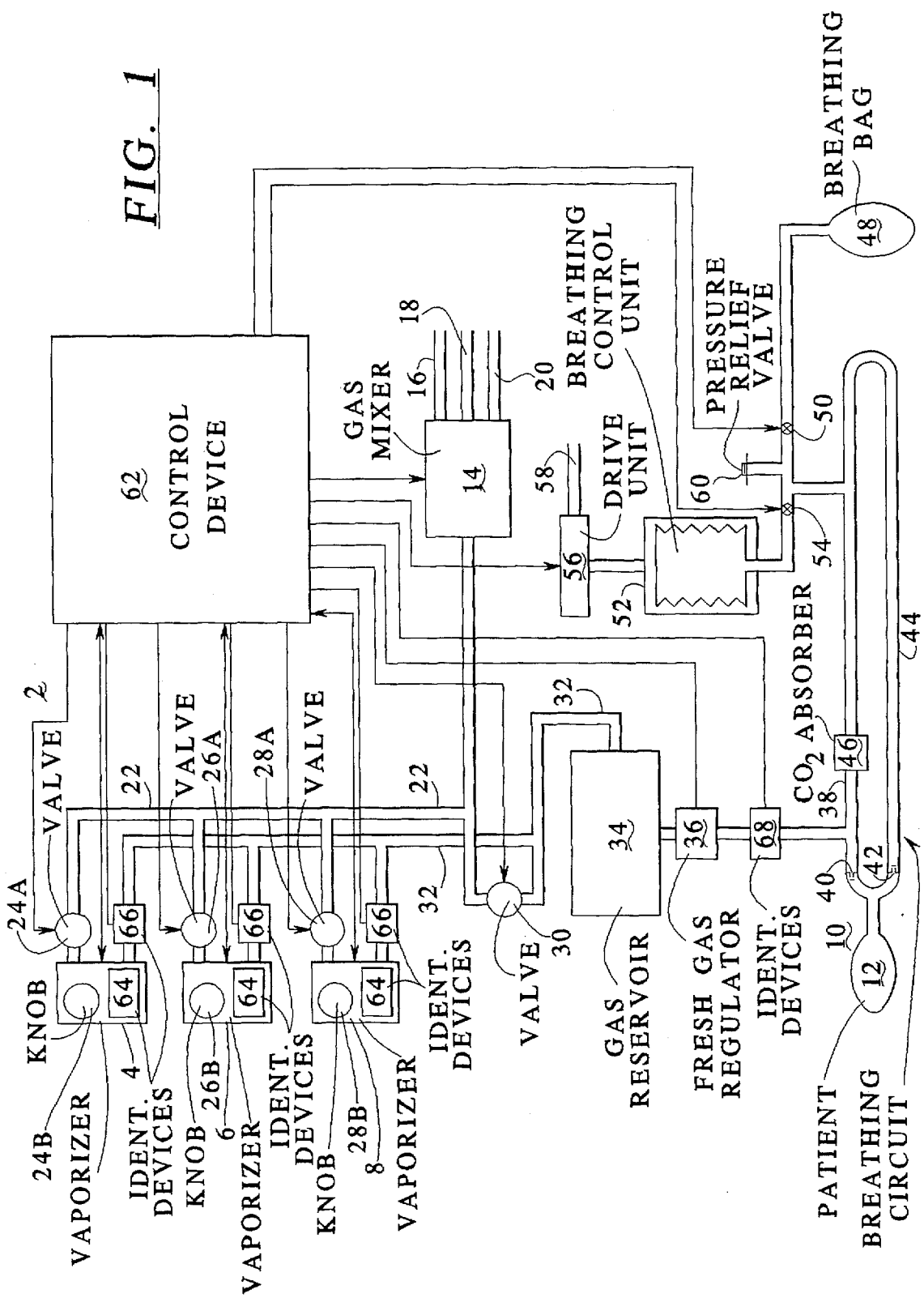
FIG. 1 shows an anaesthetic system incorporating an anesthetic identification device constructed and operating according to the principles of the present invention.

FIG. 1 shows anaesthetic system 2 to which a first anaesthetic vaporizer 4, a second anaesthetic vaporizer 6 and a third anaesthetic vaporizer 8 are connected to selectively supply an anaesthetic to a breathing circuit 10. 5 The breathing circuit 10 then supplies a patient 12 with a breathing gas containing anaesthetic gas.

The breathing gas is fed to the anaesthetic system 2 via a gas mixer 14. Gas can be carried to the gas mixer 14 via a 10 first gas connection 16, a second gas connection 18 and a third gas connection 20. The supplied gases can consist of air, nitrous oxide and oxygen. If only oxygen and nitrous oxide are to be supplied to the anaesthetic system 2, the third gas connection 20 can either be kept closed or also used for supplying oxygen. Supplying oxygen via two separate gas connections enhances patient safety. The incoming gases are mixed in the gas mixer 14 in selectable proportions to form a breathing gas with a specific pressure, a specific flow of the mixed breathing gas then being carried through a first gas line 22 to the anaesthetic vaporizers 4, 6 and 8.

A first blocking valve 24A is arranged next to the first anaesthetic vaporizer 4. The first blocking valve 24A, which is normally closed, keeps gas from the first gas line 22 from passing through the first anaesthetic vaporizer 4. When a first setting knob 24B on the first anaesthetic vaporizer 4 is activated by an operator, the first blocking valve 24A opens, and the liquid anaesthetic in the first anaesthetic vaporizer 4 is vaporized in order to produce the selected concentration of anaesthetic in the breathing gas. In the corresponding manner, a second blocking valve 26A is arranged next to the second anaesthetic vaporizer 6, and a third blocking valve 28A is arranged next to the third anaesthetic vaporizer 8. The second blocking valve 26A opens when a second setting know 26B on the second anaesthetic vaporizer 6 is activated, and the third blocking valve 28A opens when a third setting knob 28B on the third anaesthetic vaporizer 8 is activated. The three blocking valves 24A, 26A and 26C are regulated so only one can be activated at a time.

A fourth blocking valve 30 is arranged next to the first gas line 22 to pass a flow of gas which has not passed through any of the anaesthetic vaporizers 4, 6 and 8.

The anaesthetic system 2 is devised so the fourth blocking valve 30 automatically opens if the first blocking valve 24A, the second blocking valve 26A and the third blocking valve 28A are closed. This ensures that the patient is supplied with breathing gas in every situation.

Breathing gas from the gas mixer 14 then passes, with or without anaesthetic gas, through a second gas line 32 to a gas reservoir 34. The breathing gas is further mixed in the gas reservoir 34, so vaporized anaesthetic is mixed with breathing gas as thoroughly as possible before being fed to the breathing circuit 10.

The breathing circuit 10 consists of a recirculating breathing circuit in which the patient 12 re-breathes a large or small part of the gas in the breathing circuit 10. The ready-mixed breathing gas in the gas reservoir 34 can be suitably referred to as fresh gas for the breathing circuit 10. Fresh gas is supplied to the breathing circuit 10 to compensate for gas losses, or gas releases, from the breathing circuit 10, e.g., by the intake of oxygen and anaesthetic gas by the patient 12 and leakage in the complete circuit system (the breathing circuit 10 and the patient 12).

The supply of fresh gas to the breathing circuit 10 is regulated by a fresh gas regulator 36. Fresh gas is carried to an inspiratory line 38 in the breathing circuit 10 and is delivered to the patient 12 through a first check valve 40. Expired gas is carried from the patient 12 through a second check valve 42 and an expiratory line 44. A carbon dioxide absorber 46 is also arranged in the breathing circuit 10.

Two possible drive systems for breathing gas in the breathing circuit 10 are shown in FIG. 1. The first consists of a manually operable breathing bag 48 which, via a valve 50, can be connected to the breathing circuit 10. when the breathing bag 48 is connected to the breathing circuit 10, a doctor can manually squeeze the breathing bag 48 to control the patient's 12 inspiration and expiration. Alternatively, a breathing control unit 52, consisting of a bellows in a container, which can be connected to the breathing circuit 10 via a valve 54, can mechanically act on the gas in the breathing circuit 10. Regulation of the breathing control unit 52 is provided by a drive unit 56 which, using compressed air from a fourth gas connection 58, can send a drive gas to the breathing control unit 52 and also can divert drive gas from the breathing control unit 52. Surplus gas in the breathing circuit 10 is removed through a pressure relief valve 60.

The anaesthetic system 2 is controlled and monitored by a control device 62. The control device 62 therefore regulates the operation of the gas mixer 14, drive unit 56, fresh gas regulator 36, blocking valves 24A, 26A, 28A, 30 and the anaesthetic vaporizers 4, 6, 8. The control device 62 also receives the functional information set by staff as to e.g., breathing rate, desired tidal volume, composition of the breathing gas etc. Other functions of the control device 56 will be apparent from the following.

The anaesthetic system 2 contains one or more anaesthetic identification devices 64, 66 and/or 68 for identifying the anaesthetics connected to it. Placement of the devices 64, 66 and 68 can vary, depending on whether liquid or gaseous anaesthetic is to be identified.

If identification of liquid anaesthetics is to be performed, a device 64 is placed in each anaesthetic vaporizer 4, 6 and 8.

A number of options are available for identifying gaseous anaesthetics. Identification can be carried out immediately after the anaesthetic vaporizers 4, 6 and 8, as illustrated with the devices 66, or immediately before the fresh gas is supplied to the breathing circuit 10, as illustrated with the device 68.

In the latter instance, one device 68 is sufficient for identifying anaesthetics from all the anaesthetic vaporizers 4, 6 and 8. The device 68 can also be placed in the breathing circuit 10, in which measurement of the concentration of anaesthetic is desired, since the gas at that location is the gas breathed by the patient. However, this placement has disadvantages, however, because an incorrect anaesthetic, the wrong concentration or a mixture of anaesthetics would have time to reach the patient 12 before identification has occurred and because moisture can condense in the breathing circuit 10 and make determination of the condensation point temperature more difficult.

Information about the anaesthetic in the anaesthetic system 2 is sent to the control device 62 in which control and alarm 30 systems can ensure that the correct anaesthetic is supplied to the patient 12 in the right concentration.

Figure 2:
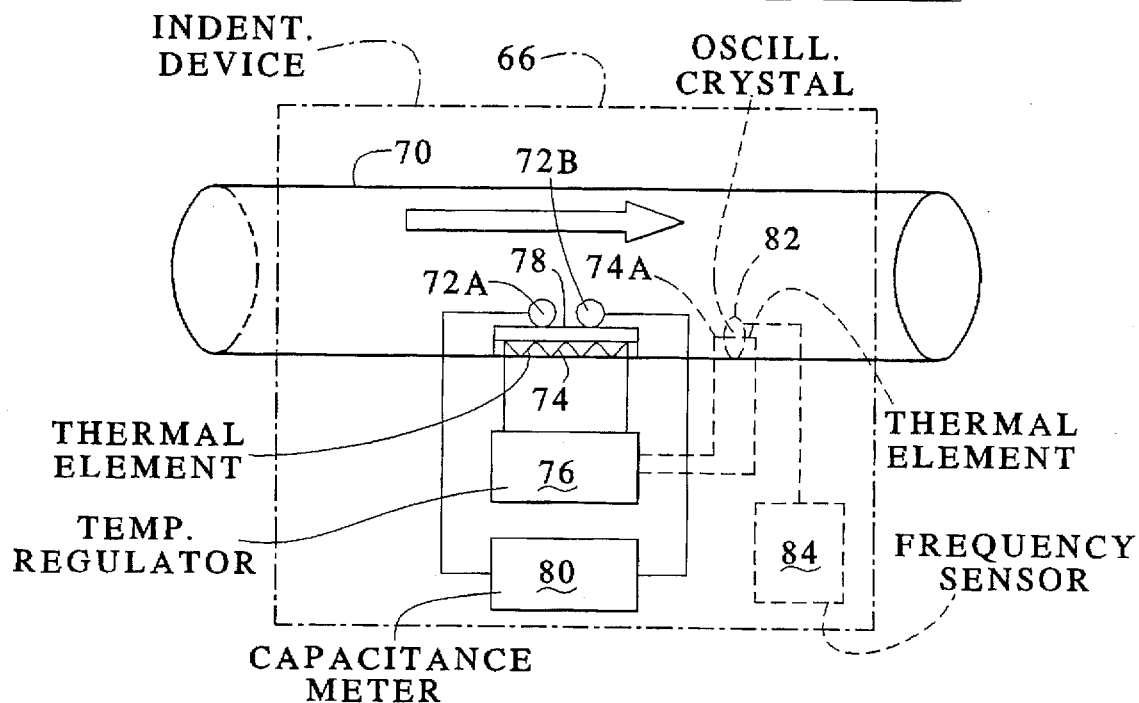
FIG. 2 shows a first embodiment of an anaesthetic identification device constructed and operating according to the principles of the present invention.

FIG. 2 is a schematic diagram of a first embodiment of the device 66 for identifying anaesthetic in the anaesthetic system 2 immediately after the anaesthetic vaporizers 4, 6 and 8.

The device 66 has a tube 70 through which anaesthetic gas is fed in the direction shown by the arrow. Some or all of the vaporized anaesthetic gas passes through the tube 70. The gas passing through the tube 70 has known pressure and flow characteristics which are regulated in the gas mixer 14 in the anaesthetic system 2 (FIG. 1), and is, in this instance, saturated with gaseous anaesthetic. The quantity and concentration of the anaesthetic in this gas mixture thus are known.

A thermal element 74 is arranged in the tube 70 to vary the temperature of a surface 78 in the tube 70. The thermal element 74 is regulated by a temperature regulator 76. The temperature variation on the surface 78 causes a gaseous anaesthetic to condense on that surface.

The capacitance between two conductors 72A and 72B (shown over-sized in FIG. 3 for legibility) changes when anaesthetic condenses on the surface 78, and this change is measured with a capacitance meter 80 connected to the conductors 72A and 72B. Since known anaesthetics have different condensation point temperatures, identifying a specific anaesthetic gas passing through the tube 70 is easy.

If there is a mixture of two anaesthetics, a secondary condensation will be detected, and both anaesthetics in the mixture will be identified. In the latter instance, an alarm 30 should be sounded or gas delivery to the patient should be immediately terminated, since an anaesthetic vaporizer must not contain more than one anaesthetic.

An oscillating crystal 82 can be used, instead of a capacitance meter, for identifying the condensation of an anaesthetic gas. This is schematically shown in FIG. 2 with dashed lines, the oscillating crystal 82 being thermally connected to a thermal element 74A. A frequency sensor 84 is connected to the oscillating crystal 82 to sense changes in its resonant frequency. When anaesthetic condenses on the oscillating crystal 82, the crystals resonance frequency changes considerably, the temperature of the thermal element 74 is then the condensation point temperature. A number of measurements of the condensation point temperature can be made, an average for the measured condensation point temperatures then being determined and used in the identification of the anaesthetic.

Figure 3:
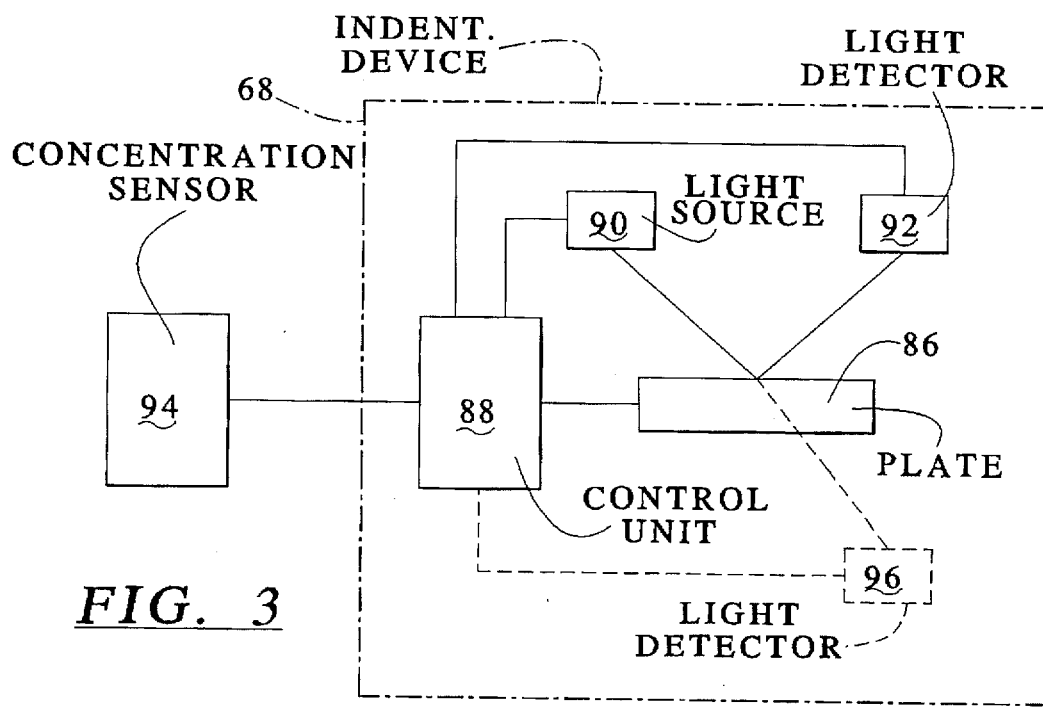
FIG. 3 shows a second embodiment of an anaesthetic identification device constructed and operating according to the principles of the present invention.

FIG. 3 schematically depicts the device 68 located at the fresh gas inlet to the inspiratory line 38 in the anaesthetic system 2. The device 68 performs optical detection of condensation. A plate 86 is arranged so the anaesthetic gas can flow over it.

The temperature of the plate 86 is regulated by a control unit 88, and the temperature is made to vary between two defined values. The plate 86 is reflective, and a light source 90 is arranged over the plate 86. The light source 90 generates a light beam aimed at the plate 86 from which the beam is reflected. The reflected light beam strikes a light detector 92. The intensity of the reflected light beam can be measured by the light detector 92.

The light source 90 is regulated by the control unit 88, and the light detector 92 is connected to the control unit 88 to send a measurement signal thereto. When anaesthetic gas condenses on the surface of the plate 86, the plate's reflectivity changes, and intensity changes are sensed by the light detector 92. The control unit 88 also receives information from an anaesthetic gas concentration sensor 94 about the concentration of anaesthetic gas in the breathing gas. This sensor signal can be a signal which indicates the continued presence of a defined concentration, the signal changing only upon a deviation from the defined concentration, provided the anaesthetic vaporizers 4, 6, 8 are sufficiently accurate in the vaporization of liquid anaesthetic. The anaesthetic gas concentration sensor 94 can alternatively be a concentration meter, arranged in conjunction with the device 68 or in the breathing circuit 10 of the anaesthetic system 2.

An alternative optical method is designated with dashed lines in FIG. 3. In the alternative optical method, the plate 86 is transparent to the light beam from the light source 90, and the intensity of the transmitted light beam is measured in an additional light detector 96. The intensity of the transmitted light beam drops when there is condensation on the plate, a clear indication of the condensation point.

In the optical embodiments, it may be advantageous to perform a number of measurements of the condensation point temperature and calculate an average value for the condensation point temperature in the determination of the anaesthetic's identity.

Figure 4:
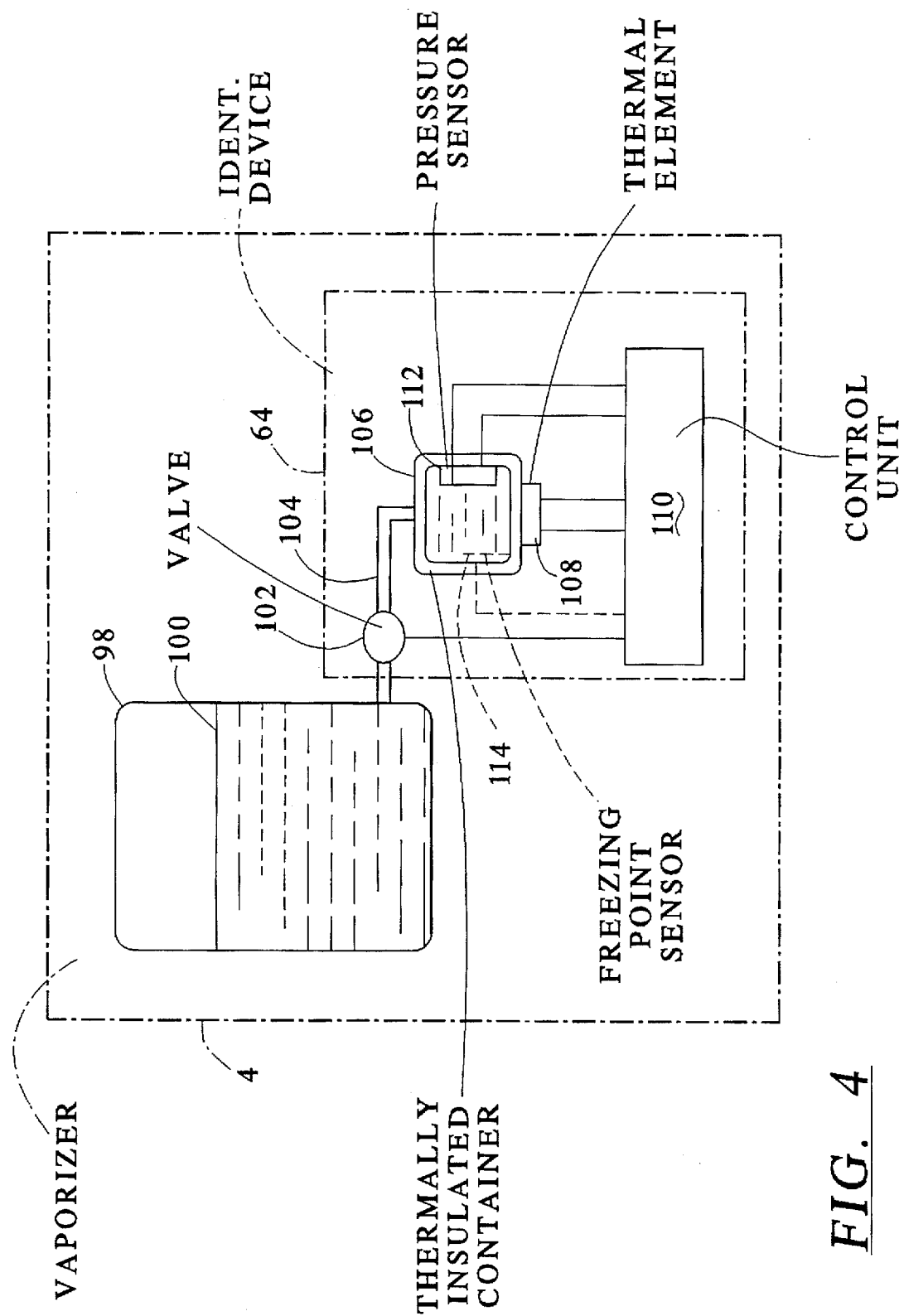
FIG. 4 shows a third embodiment of an anaesthetic device constructed and operating according to the principles of the present invention.

A third embodiment of the device 64 is schematically depicted in FIG. 4. The device 64 is placed in an anaesthetic vaporizer 4 and performs identification of liquid anaesthetic. A container 98 for holding liquid anaesthetic 100 is arranged in the anaesthetic vaporizer 4. The device 64 is connected to this container 98 so that liquid anaesthetic 100 can be carried to a thermally insulated container 106, via a valve 102 and tube 104. The temperature in the thermally insulated container 106 can be varied with a thermal element 108 regulated by a control unit 110.

When an exact volume of liquid anaesthetic 100 has been transferred to the thermally insulated container 106, the valve 102 is closed, and the temperature in the thermally insulated container 106 is raised. When the boiling point temperature of the liquid anaesthetic 100 is reached, pressure in the thermally insulated container 106 rises sharply. This rise is sensed by a pressure sensor 112, also connected to the control unit 110. In this manner, the boiling point temperature of liquid anaesthetic 100 can be rapidly and reliably established, and the identity of the anaesthetic can then be determined from the boiling point temperature.

Identification of the anaesthetic can be performed e.g. every time the vaporizer is activated or filled with fresh anaesthetic. The liquid anaesthetic carried from the container 98 to the thermally insulated container 106 can either be returned to the container 98 or passed on for vaporization in some manner not shown.

Alternatively, a small, predefined volume of liquid anaesthetic can be sent to a closable vessel and heated until it completely changes to the gaseous state. Again, the boiling point temperature can be determined by measurement of pressure in the vessel.

Another version of the device 64 is shown with dashed lines in FIG. 4. The freezing point of the liquid anaesthetic 100 can be determined instead of its boiling point temperature. The thermal element 108 is regulated so that the temperature drops toward the freezing point of liquid anaesthetics. A freezing point detector 114 is arranged in the thermally insulated container 106 to sense when the liquid anaesthetic 100 has frozen. This identification can, e.g., be based on sensing of when sufficiently large crystals of anaesthetic have formed or when the liquid anaesthetic has completely frozen. The freezing point temperature, like the boiling point temperature, is unique for each liquid anaesthetic, so identification is simple once the freezing point temperature 5 has been established.

All the devices described herein have in common a need for the condensation point temperature, the boiling point temperature and the freezing point temperature to be established in an identical manner with known anaesthetics so the best possible reference values are obtained, i.e., the devices 64, 66 and 68 should be calibrated under known conditions.

The indicated locations for the devices 66 and 68 are not invariable. In principle, the devices can be located anywhere in the part of the anaesthetic system 2 in which anaesthetic gas is present. However, they should not be located so water vapor simultaneously occurs with the gas mixture, since the water vapor could condense and impair identification of the condensation point for the anaesthetic.

Other transitions between different physical states, such as the melting point temperature, could also be used in the corresponding manner for determining the identity of an anaesthetic. Combinations of two or more transitions can also be used. For example, both the freezing point and melting point, or the boiling point and the condensation point, can be determined. Since only a small amount of liquid anaesthetic is diverted, all transitions to different physical states can be determined relatively quickly, i.e. temperature can be varied so the anaesthetic in this first physical state vaporizes, condenses, freezes and/or melts before again returning to its first physical state.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for identifying an anaesthetic in an anaesthetic system, comprising the steps of:

varying a temperature of at least a sample of an anaesthetic and thereby causing said anaesthetic to change from a first physical state to a second physical state;

determining a transition temperature at which the change from said first physical state to said second physical state occurs; and identifying said anaesthetic from said transition temperature.

2. A method as claimed in claim 1 wherein said anaesthetic in said first physical state is a gaseous anaesthetic, and wherein said second physical state is a liquid state, and wherein said transition temperature is a condensation point temperature, and wherein the step of varying the temperature comprises varying the temperature of at least a sample of the gaseous anaesthetic and thereby condensing at least some of said gaseous anaesthetic, wherein the step of determining said transition temperature comprises determining said condensation point temperature, and wherein the step of identifying said anaesthetic comprises identifying said anaesthetic from said condensation point temperature.

3. A method as claimed in claim 1 wherein said anaesthetic in said first physical state is a liquid anaesthetic, wherein said second physical state is a solid, and wherein said transition temperature comprises a freezing point temperature, wherein the step of varying the temperature comprises varying the temperature for freezing at least some of said liquid anaesthetic, wherein the step of identifying the transition temperature comprises identifying the freezing point temperature, and wherein the step of identifying the anaesthetic comprises identifying the anaesthetic from said freezing point temperature.

4. A method as claimed in claim I wherein said anaesthetic in said first physical state is a liquid anaesthetic, wherein said second physical state is a gas, and wherein said transition temperature is a boiling point temperature, and wherein the step of varying said temperature comprises varying the temperature for boiling at least some of said liquid anaesthetic, wherein the step of determining the transition temperature comprises determining the boiling point temperature, and wherein the step of identifying the anaesthetic comprises identifying the anaesthetic from said boiling point temperature.

5. An anaesthetic system comprising:

means for varying a temperature of at least a sample of an anaesthetic for causing said anaesthetic to change from a first physical state to a second physical state;

physical state-sensitive means for determining a transition temperature at which said anaesthetic changes from said first physical state to said second physical state; and means for identifying said anaesthetic from said transition temperature.

6. An anaesthetic system as claimed in claim 5 wherein said means for varying the temperature of said anaesthetic comprises a thermal element to which said at least a sample of said anaesthetic is exposed, and control means connected to said thermal element for operating said thermal element for varying the temperature of the anaesthetic.

7. An anaesthetic system as claimed in claim 6 wherein said anaesthetic in said first physical state is a gaseous anaesthetic, wherein said control means comprises means for operating said thermal element for varying the temperature of the gaseous anaesthetic within a predetermined temperature range, wherein said physical state-sensitive means comprises condensation detector means connected to said control means for sensing when condensation of said gaseous anaesthetic occurs and for determining said transition temperature as a condensation point temperature of said gaseous anaesthetic, and wherein said means for identifying said anaesthetic comprises means for identifying said anaesthetic from said condensation point temperature.

8. An anaesthetic system as claimed in claim 7 wherein said condensation detector means comprises a surface on which condensation of said anaesthetic occurs, and means for sensing condensation by measuring a change in an electrical property caused by condensation of said anaesthetic on said surface.

9. An anaesthetic system as claimed in claim 8 wherein said means for measuring a change in an electrical property comprises means for measuring a change in capacitance caused by condensation of said anaesthetic on said surface.

10. An anaesthetic system as claimed in claim 7 wherein said condensation detector means comprises an oscillating crystal on which said gaseous anaesthetic condenses, said oscillating crystal having a resonant frequency, and means for detecting a change in said resonant frequency of said crystal due to the condensation of said gaseous anaesthetic thereon.

11. An anaesthetic system as claimed in claim 7 wherein said condensation detector means comprises optical detector means for sensing when condensation of said gaseous anaesthetic occurs.

12. An anaesthetic system as claimed in claim 11 wherein said optical detector means comprises a reflective surface on which said gaseous anaesthetic condenses, light source means for emitting a beam of light at said reflective surface and thereby producing a reflected light beam, said reflected light beam having an intensity which changes dependent on condensed anaesthetic on said reflective surface, and light detector means for measuring the intensity of the reflected light beam and for generating a signal indicating condensation of said anaesthetic has occurred when said intensity of said reflected light beam exhibits a predetermined change.

13. An anaesthetic system as claimed in claim 11 wherein said optical detector means comprises a transmissive surface on which said gaseous anaesthetic condenses, light source means for emitting a beam of light at said transmissive surface and thereby producing a transmitted light beam, said transmitted light beam having an intensity which changes dependent on condensed anaesthetic on said transmissive surface, and light detector means for measuring the intensity of the transmitted light beam and for generating a signal indicating condensation of said anaesthetic has occurred when said intensity of said transmitted light beam exhibits a predetermined change.

14. An anaesthetic system as claimed in claim 6 wherein said anaesthetic in said first physical state is a liquid anaesthetic, wherein said control means comprises means for regulating the temperature of said thermal element within a predetermined temperature range, wherein said physical state-sensitive means comprises a freezing point detector connected to said control means for sensing when said liquid anaesthetic freezes for identifying said transition temperature as a temperature of said thermal element at which a predetermined amount of frozen anaesthetic has been sensed, and wherein said means for identifying said anaesthetic comprises means for identifying said anaesthetic from said freezing point temperature.

15. An anaesthetic system as claimed in claim 6 wherein said anaesthetic in said first physical state comprises a liquid anaesthetic, said anaesthetic system further comprising a vessel for receiving a predetermined amount of said liquid anaesthetic, said vessel being in thermal contact with said thermal element, wherein said control means comprises means for regulating said temperature of said thermal element within a predetermined temperature range, wherein said physical state-sensitive means comprises a pressure meter connected to said vessel for sensing when said liquid anaesthetic begins to boil and for determining said transition temperature as a boiling point of said anaesthetic in said vessel when a predetermined increase in the pressure in said vessel is sensed, and wherein said means for identifying the anaesthetic comprises means for identifying the anaesthetic from the boiling point temperature.

16. An anaesthetic system as claimed in claim 6 further comprising a breathing circuit adapted for administering anaesthetic to a patient;
   means for supplying a breathing gas containing said anaesthetic to said breathing circuit;
   a concentration meter connected in said breathing circuit for measuring a concentration of said anaesthetic, and wherein said means for identifying said anaesthetic comprises means for identifying said anaesthetic from said condensation point and said concentration.

* * * * *